United States Patent [19]

Fuisz

[11] Patent Number: 5,728,397
[45] Date of Patent: Mar. 17, 1998

[54] POLYDEXTROSE PRODUCT AND PROCESS

[75] Inventor: Richard C. Fuisz, Great Falls, Va.

[73] Assignee: Fuisz Technologies Ltd., Chantilly, Va.

[21] Appl. No.: 795,451

[22] Filed: Feb. 4, 1997

Related U.S. Application Data

[63] Continuation of Ser. No. 19,097, Feb. 18, 1993, abandoned, which is a continuation-in-part of Ser. No. 881,612, May 12, 1992, abandoned.

[51] Int. Cl.$^6$ .................... A61K 9/00; A61K 9/16
[52] U.S. Cl. .................... 424/439; 424/401; 536/123.1; 536/123.13; 536/126
[58] Field of Search .................... 424/401, 459; 536/123.1, 123.13, 126

[56] References Cited

U.S. PATENT DOCUMENTS

| | | | |
|---|---|---|---|
| 1,489,342 | 4/1924 | Brent | 425/9 |
| 2,826,169 | 3/1958 | Le Veen | 24/79.4 |
| 2,918,404 | 12/1959 | Mende et al. | 514/683 |
| 3,019,745 | 2/1962 | Du Bois et al. | 425/9 |
| 3,036,532 | 5/1962 | Bowe | 425/9 |
| 3,067,743 | 12/1962 | Merton et al. | 424/431 |
| 3,070,045 | 12/1962 | Bowe | 425/9 |
| 3,073,262 | 1/1963 | Bowe | 425/9 |
| 3,095,258 | 6/1963 | Scott | 264/177.14 |
| 3,131,428 | 5/1964 | Mika | 267/177.13 |
| 3,308,221 | 3/1967 | Opfell | 264/174 |
| 3,324,061 | 6/1967 | Tanquary et al. | 264/211.17 |
| 3,557,717 | 1/1971 | Chivers | 107/54 |
| 3,595,675 | 7/1971 | Ash et al. | 99/130 |
| 3,615,671 | 10/1971 | Schoaf | 99/78 |
| 3,625,214 | 12/1971 | Higuchi | 128/260 |
| 3,723,134 | 3/1973 | Chivers | 99/134 |
| 3,762,846 | 10/1973 | Chivers | 425/7 |
| 3,766,165 | 10/1973 | Rennhard | 260/209 |
| 3,856,443 | 12/1974 | Salvi | 425/9 |
| 3,875,300 | 4/1975 | Homm et al. | 424/28 |
| 3,876,794 | 4/1975 | Rennhard | 424/152 |
| 3,925,525 | 12/1975 | LaNieve | 264/40 |
| 3,930,043 | 12/1975 | Warning et al. | 426/515 |
| 3,951,821 | 4/1976 | Davidson | 252/1 |
| 3,967,623 | 7/1976 | Butterworth et al. | 128/287 |
| 3,992,265 | 11/1976 | Hansen | 195/127 |
| 4,090,920 | 5/1978 | Studer, Jr. | 195/127 |
| 4,136,145 | 1/1979 | Fuchs et al. | 264/164 |
| 4,153,512 | 5/1979 | Messner et al. | 195/103.5 |
| 4,293,570 | 10/1981 | Vadasz | 426/3 |
| 4,303,684 | 12/1981 | Pitchon et al. | 426/312 |
| 4,371,516 | 2/1983 | Gregory et al. | 424/22 |
| 4,376,743 | 3/1983 | Dees | 264/103 |
| 4,492,685 | 1/1985 | Keith et al. | 424/28 |
| 4,496,592 | 1/1985 | Kuwahara et al. | 426/5 |
| 4,500,546 | 2/1985 | Turbak et al. | 514/781 |
| 4,526,525 | 7/1985 | Oiso et al. | 425/9 |
| 4,585,797 | 4/1986 | Cioca | 514/773 |
| 4,619,833 | 10/1986 | Anderson | 426/548 |
| 4,793,782 | 12/1988 | Sullivan | 425/7 |
| 4,855,326 | 8/1989 | Fuisz | 514/53 |
| 4,873,085 | 10/1989 | Fuisz | 424/400 |
| 4,879,108 | 11/1989 | Yang et al. | 424/400 |
| 4,885,281 | 12/1989 | Hanstein et al. | 514/777 |
| 4,978,537 | 12/1990 | Song | 426/5 |
| 4,997,856 | 3/1991 | Fuisz | 514/777 |
| 5,011,532 | 4/1991 | Fuisz | 106/215 |

(List continued on next page.)

FOREIGN PATENT DOCUMENTS

| | | |
|---|---|---|
| 88/2770 | 4/1988 | South Africa. |
| 88/2771 | 4/1988 | South Africa. |
| 89/9318 | 12/1989 | South Africa. |
| 90/2139 | 3/1990 | South Africa. |
| 90/8406 | 8/1991 | South Africa. |

*Primary Examiner*—Sally Gardner-Lane
*Attorney, Agent, or Firm*—John F. Levis; Hoffman & Baron

[57] ABSTRACT

The present invention is a process for manufacturing polydextrose polymerizate by subjecting flowable new polydextrose feedstock to flash shear under conditions which provides instantaneous formation of separate masses of solid polydextrose. The present invention also includes the product resulting therefrom.

7 Claims, 4 Drawing Sheets

U.S. PATENT DOCUMENTS

| | | | |
|---|---|---|---|
| 5,028,632 | 7/1991 | Fuisz | 514/772 |
| 5,034,421 | 7/1991 | Fuisz | 514/772 |
| 5,096,492 | 3/1992 | Fuisz | 106/215 |
| 5,279,849 | 1/1994 | Fuisz et al. | 426/658 |
| 5,346,377 | 9/1994 | Bogue et al. | 425/6 |
| 5,387,431 | 2/1995 | Fuisz | 426/658 |
| 5,429,836 | 7/1995 | Fuisz | 426/601 |
| 5,597,608 | 1/1997 | Fuisz | 426/658 |

POLYDEXTROSE PRODUCT AND PROCESS

BACKGROUND OF THE INVENTION

This application is a continuation of application Ser. No. 08/019,097, filed on Feb. 18, 1993, now abandoned, which is a Continuation-in-part application of U.S. application Ser. No. 881,612 filed May 12, 1992, now abandoned. The present invention relates to a new process for producing polydextrose and the product prepared thereby.

Polydextrose is a non-sucrose, essentially non-nutritive carbohydrate substitute. Polydextrose can be prepared through polymerization of glucose in the presence of polycarboxylic acid catalysts and polyols. Generally, polydextrose is known to be commercially available in three forms: polydextrose A and polydextrose K, which are powdered solids, and polydextrose N supplied as a 70% solution. Each of these products also contain some low molecular weight components, such as glucose, sorbitol and certain oligomers.

Most of the interest in polydextrose has centered around its use in various edible compositions. For example, polydextrose has stimulated interest in the food arts as a low-calorie bulking agent or as a part of many low-calorie or light foods since it has only about one-quarter of the calories of sucrose. Non-food related uses for the material have largely been ignored.

Unfortunately, the ability to disperse polydextrose and use it in different products has been limited by certain physical and chemical phenomena. Unlike most saccharide products, it is relatively unreactive and physically resistive to mixing and dispersing. While artisans have been able to process sugar to enhance its utility in food and other products, polydextrose heretofore did not appear to be as versatile.

Moreover, certain difficulties are incurred in the production of polydextrose which create inefficiency and waste and contribute to its lack of versatility as a commodity. U.S. Pat. Nos. 3,766,165 and 3,876,794 describe a method for making polydextrose. Generally, polydextrose is manufactured by anhydrous melt polymerization of glucose and maltose using edible acids as catalysts and as cross-linking agents. The polymer produced from the reaction is cooled, crystallized and milled. Milling of the solidified polymer results in loss of product in the form of unwanted fines which are produced during milling. It is believed that up to 20% of the product can be lost as a result of the production of fines. Moreover, milling is an energy-intensive procedure which detracts from the overall efficiency of the process for manufacturing polydextrose, and the form of the product is limited to ground solid polymer, which is usually a powder. Thus, the present process for manufacturing polydextrose for commercial sale and use is severely limited.

In commonly-owned copending applications Ser. No. 881,603 filed May 12, 1992 a process for producing a modified polydextrose is disclosed wherein solid polydextrose is spun in a cotton candy type machine to provide a solid polydextrose product which is different from the solid polydextrose feedstock. Similarly, parent U.S. application Ser. No. 881,612 filed May 12, 1992 describes a pharmaceutical composition made from a solid polydextrose feedstock and a medicament. The resulting composition is a second solid which has been transformed by spinning a first solid polydextrose feedstock manufactured by the procedure set forth above, i.e., by milling a solid polymer.

Other references which disclose processing by spinning a solid feedstock are commonly-assigned U.S. Pat. No. 4,855, 326 and U.S. Pat. No. 4,873,085, both issued to Fuisz. These patents are directed to products which include various active agents, having pharmacological and/or cosmetic properties, combined with readily water-soluble melt-spinnable materials such as sugars or cellulosic substances. The active agents spun with these materials demonstrate enhanced solubility.

Other disclosures are commonly-assigned U.S. Pat. Nos. 5,011,532 and 5,096,492 which contain examples where oleaginous substances are mixed with sugar and melt-spun. The spun products disperse readily in water, forming colloidal or pseudo-colloidal dispersions. The '532 patent explains how oleaginous substances such as vegetable oil, mineral oil, baby oil, margarine, lanolin, cocoa butter and the like, which characteristically have little or no affinity for water, can be rendered dispersible by mixing the oleaginous substance with sugar and melt-spinning the mixture in a cotton candy spinning machine or equivalent.

Other disclosures dealing with spinning substances with one or more sugars will be found in commonly-assigned U.S. Pat. Nos. 4,873,085; 4,997,856; 5,028,632 and 5,034, 421. Generally, each of these disclosures are directed to melt-spinning sugar by introducing sugar and various ingredients into a cotton candy spinning machine. Such equipment is normally operated at a temperature of around 200° C. and at speeds of about 3,500 r.p.m. Melt-spinning in such equipment relies upon certain characteristics of sucrose, such as high crystallinity and high physical and chemical lability. The spun products disclosed in these patents and described as taking the form of a floss or mass of spun fibers.

The disclosures set forth above relate to transforming a solid feedstock material having a first structure to a second solid having a structure which is altered from the first structure. None of these disclosures addresses the difficulties incurred in producing polydextrose as a commercial commodity.

It is, therefore an object of the present invention to provide a process for overcoming some of the shortcomings found in present polydextrose manufacturing procedures and the products resulting therefrom. Other and further objects will become known to those skilled in the art as the invention is described herein.

SUMMARY OF THE INVENTION

The present invention is a process for manufacturing polydextrose by subjecting flowable polydextrose feedstock to flash shear under conditions which provide instantaneous formation of separate masses of solid polydextrose. "Flowable polydextrose feedstock" results directly from a polydextrose polymerization reaction and is maintained in flowable condition without solidification. As used herein "flowable polydextrose feedstock" means that the polymer has not yet been solidified or crystallized before disrupting by use of flash shear.

Polymerizate is used in the present application to mean the product of a polymerization reaction which has not undergone solidification. Polymerizate includes solid product resulting from the process as well as product in free-flow condition after it has been disrupted by shear.

One embodiment of the present invention contemplates subjecting the feedstock to flash shear by directing it from the polymerization reactor to a spinning apparatus, such as a cotton candy type spinning machine, which provides shear force and separation whereby separate polydextrose masses are formed.

In an alternative embodiment, flash shear is provided by directing the new polydextrose feedstock stream under pressure to an exit orifice. A disruptive fluid shear force is applied to the feedstock stream to separate it and permit it to solidify in the multiple masses of polydextrose matrix.

In all embodiments flowable polydextrose feedstock is maintained in the flowable state from polymerization reaction to flash shear. Accordingly, it may be necessary to provide apparatus to provide added heat under controlled conditions to ensure maintenance of flow.

In a preferred embodiment of the present invention an additional ingredient may be introduced to the polymerizate prior to subjecting it to shear. For example, the additional ingredient or ingredients can be injected into the stream after the polymerization reaction. It is also contemplated that the additional ingredient or ingredients can be incorporated before or during polymerization. Additional ingredients include, but are not limited to, oleaginous material, flavors, and fragrances.

The present invention also contemplates a new polydextrose polymerizate which is prepared directly from a flowable polydextrose stream resulting from a polymerization reaction. The product is a discontinuous polydextrose matrix having a morphology resulting from subjecting the flowable feedstock to shear conditions which provide separate masses of solid polydextrose matrix. It is also contemplated that at least one additional ingredient (or more than one ingredient) can be added while in the flowable stage. Alternatively, at least one additional ingredient can be added prior to or during the polymerization reaction.

Yet another aspect of the invention is an apparatus for manufacturing new polydextrose polymerizate which includes a reaction chamber having means for controlling the temperature, pressure, and moisture content of the polymerization reaction environment within the chamber, and a means for advancing contents of the chamber therefrom. The apparatus also includes means for conveying the contents of the polymerization chamber which is in fluid communication therewith. The means for conveying also has the capability of controlling the conditions of temperature, pressure and moisture as the contents is moved through the conveyance means. Finally, the apparatus includes a means for shearing polydextrose melt and permitting free-flow formation of discreet masses of polydextrose polymerizate.

As a result of the present invention, a commercial polydextrose product can be provided without undergoing the requirement of high intensity milling which is necessary to reduce solid polymer to a flowable powder. Consequently, the loss of fines, generally associated with milling, is eliminated. In addition, the morphology of the solid particle produced can be changed by controlling processing conditions.

Furthermore, a useful polydextrose product is formed which can be readily used without further processing alone or in combination with other ingredients. The applications for these polydextrose containing materials are vast.

As a consequence, polydextrose can be readily supplied without need for the energy-intensive and inefficient procedures normally associated with manufacturing of polydextrose.

As another advantage, polydextrose polymer can be provided in the form of a shearform product without requiring addition of heat sufficient to reduce a solid product to flowable condition.

For better understanding of the present invention, together with other and further objects, reference is made to the following description, taken in conjunction with the accompanying drawings, and its scope will be pointed out in the appended claims.

BRIEF DESCRIPTION OF THE DRAWINGS

Preferred embodiments of the invention have been chosen for purposes of illustration and description, but are not intended in any way to restrict the scope of the present invention. The preferred embodiments are shown in the accompanying drawings, wherein.

DETAILED DESCRIPTION OF THE INVENTION

Figure 1:
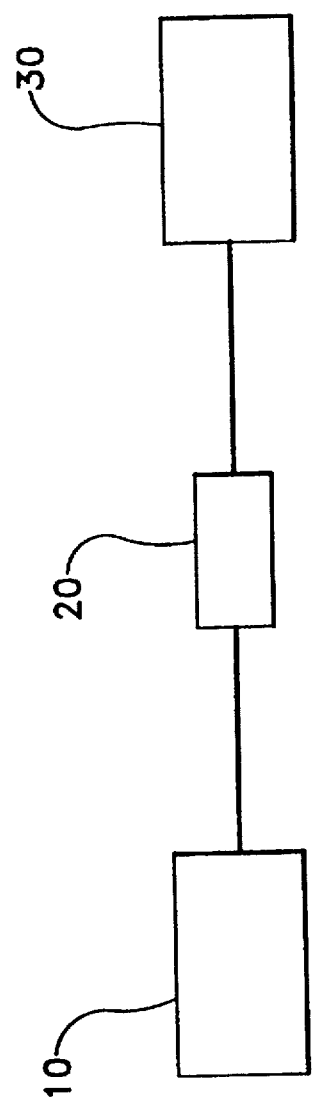
FIG. 1 is a block diagram of the process and apparatus of the present invention.

The present invention is a process for manufacturing a polydextrose product which can be readily sold and used as a commercial commodity. The product is prepared by subjecting a stream of polydextrose directly from a polydextrose polymerization reaction to a shear force which separates the stream into multiple masses of polydextrose matrix under conditions which induce solidification under free flow condition immediately after shearing.

Glucose and maltose polymers, commonly referred to as polydextrose, are produced directly from glucose and maltose by a process of anhydrous melt polymerization using edible acids as catalysts and as cross-linking agents. The starting materials used in the melt polymerization are maltose or glucose, although other simple sugars may be used as well. The sugars are provided to the process as anhydrides or dry hydrated solids, and are in powdered form.

The acids used as catalysts, cross-linking agents or polymerization activators may be any one of a series of relatively non-volatile, edible, organic polycarboxylic acids. It has been found that the following acids are useful as polymerization activators: citric, fumaric, tartaric, succinic, adipic, itaconic or terephthalic acids. The acid or anhydride must be food-acceptable, that is palatable and free of significant adverse affect at the level of ordinary use. Inorganic acids are not suitable for use as acid catalysts in anhydrous polymerization since they do not serve as cross-linking agents in the production of insoluble polydextrose. The acid selected should be relatively non-volatile, since more volatile acids may be vaporized during the heating and melting procedures which occur during polymerization. The polycarboxylic acids used are largely, but incompletely, esterified with the polydextrose in the polymerizing process, forming acid polyglucose esters or acid polymaltose esters.

The acid moieties are likely to serve as cross-linking agents between different polyglucose or polymaltose molecules in the insoluble polymers whereas, in the soluble polymers, each acid moiety is more likely to be esterified to only the polymer molecule.

The dry powdered glucose can be combined with the proper amount of acids. The acid and glucose or maltose can be heated and melted under reduced pressure. The melt should then be maintained in the absence of water until substantial polymerization occurs. The anhydrous melt polymerization should be carried out at pressures below atmospheric, preferably not to exceed 300 mm. Hg, e.g. from about $10^{-5}$ to 100 to 300 mm. Hg, and can be obtained by the use of a vacuum pump, a steam jet ejector, an aspirator or by other means. Air should be excluded from the environment of the polymerization mixture in order to minimize decomposition and discoloration of the polyglucoses or polymaltoses formed in the polymerization. A fine stream of nitrogen has been found to be useful as a method for excluding air and removing the waters of hydration and polymerization which are formed. Where the nitrogen purge is used, the vacuum requirements are lessened, but pressures of 100 to 300 mm. Hg or less are still preferred.

The duration of the reaction and the reactant temperature are interdependent variables in the operation of the polymerization. A preferable temperature for the melt polymerization is from about 140° C. to about 180° C. The precise temperature for the anhydrous melt polymerization depends on the initial ratio of glucose, maltose or other sugars to the acid which is used, the reaction time and the proportion of soluble polydextrose to insoluble, cross-linked polydextrose which is desired in the final product mixture.

The production of a large proportion of soluble glucose or maltose polymers usually requires a concentration of acid catalyst between about 0.1 and 10 mole %. Preferably the concentration is between 0.5 and 5%. As the amount of acid is increased, the degree of acid cross-linking increases and the proportion of water-insoluble polyglucose or polymaltose increases. Where acid concentrations are unnecessarily high, problems may arise with regard to neutralizing the excess acid which is present in the final product mixture. The amount of acid required for a particular polymerization, the polymerization duration, the polymerization temperature and the nature of the products desired are all interdependent. The selection of the amount of acid to be used should take into account these factors.

The thermal exposure (reaction time and temperature) used in the production of soluble polydextrose by polymerization should be as low as possible, since discoloration, caramelization and degradation increase with prolonged exposure to high temperature. With regard to the polymerization reaction, it is beneficial that as the temperature of the polymerization is increased, the time required to achieve substantially complete polymerization decreases. Therefore, the polymerization may be conducted at about 160° C. and at a reaction duration of about 8 hours, as well as at a temperature of about 140° C. and a reaction duration of about 24 hours with approximately the same resulting degree of polymerization. Comparable results are also achieved in continuous polymerization at temperatures in the range of about 200° to 300° C. in about 10 minutes or less without significant darkening while the reaction is under vacuum.

With regard to production of insoluble polydextrose, the molar ratio of glucose or maltose to acid may also be within the ranges specified above for production of soluble polysaccharides, and especially from about 2.5 to about 10 mole % of acid. It is preferable, to use molar ratios of glucose or maltose acid of between about 12:1 to about 20:1 in the production of insoluble polydextrose. These ratios are preferred in spite of the requirements of high reaction temperature and relatively long reaction times because the total yield of soluble and insoluble polydextrose is between 90 and 99% at the sugar to acid ratios. Thus, using these higher ratios, it is possible to produce in one reaction mixture a yield of between 50 and 60% of insoluble polydextrose and between about 40 and 50% of soluble polydextrose.

It is important that the time required to introduce the stream of new polydextrose feedstock to shear be minimized in order to reduce the possibility of browning, charting, or caramelization. Thus, the means for directing the feedstock stream from the reactor to the shear step must be heated and configured to minimize the residence time of exposure to high temperature.

It has also been found that inclusion of a food acceptable polyol, such as sorbitol, in the saccharide-carboxylic acid reaction mixture prior to polycondensation yields a superior product. In most cases, 90% or more of the polyol cannot be isolated from the condensation product, demonstrating that it has been chemically incorporated in the polymer. These additives function as internal plasticisers to reduce viscosity and also to provide improved color and taste. This is evident for example in the manufacture of hard candy from such condensation polymers, where the rheological properties of the melt are improved during processing. Foaming is minimized and a better tasting product of lighter color is obtained. In addition to sorbitol, other food-acceptable polyols including glycerol, erythritol, zylitol, mannitol and galactitol. Polyol concentrations of from about 5 to 20% by weight of the total reaction mixture provide such advantages, and levels of from about 8 to 12% by weight are preferred.

Chemical purification is not required for products made in accordance with the process of the present invention. Where soluble and insoluble polydextroses are produced together, separation may be desired.

Neutralization of the polydextrose may be desirable for certain applications despite the very low levels of acid catalyst employed. For example, where the polydextrose are to be used in dietetic foods containing whole milk, excess acid which may be present and the unneutralized polydextrose will tend to curdle the milk. In the case of soluble polydextrose, the solutions of polydextrose are neutralized directly. This neutralization may be accomplished by adding carbonates of potassium, sodium, calcium or magnesium to the solution of polydextrose. Where sodium and potassium are used together a physiologically balanced mixture may be used. The salt content of a typical polydextrose solution which has been adjusted to a pH of about 5 to 6 is a mere 0.5 to 1.0%. Other materials which may be used to adjust the pH of soluble polydextrose solutions include 1-lysine, d-glucosamine, N-methyl glucamine and ammonium hydroxide. The first two of these compounds are natural materials and should not be objectionable as an ingredient of dietetic foods and the last compound, which is rapidly excreted by the body in the form of urea, would not be objectionable as an ingredient in dietetic foods. N-methyl glucamine is used as solubilizing agent for pharmaceuticals and should not be objectionable as an ingredient in dietetic foods. Other methods for reducing the acidity of polydextrose solutions are dialysis and ion exchange.

Most of the polydextroses produced in this invention have an average molecular weight of from about 1,500 to about 36,000. The soluble polyglucoses which are produced have been found to have an average molecular weight of from about 1,500 to about 18,000 and the insoluble polydextroses produced have been found to have an average molecular weight of between about 6,000 and about 36,000.

The experimentally determined number average molecular weights of the polydextroses produced in this procedure are usually found to range from about 1,000 to about 24,000, with most of the molecular weights falling in the range of 4,000 to about 12,000. These number average molecular weights were determined by the modified reducing end-group method according to Isbell (J. Res. Natl. Bur. Standards 24, 241 (1940)). This method is based on the reduction of alkaline copper nitrate reagent. The number average molecular weight values are computed on the basis of standardization with gentiobiose, assuming that equimolar quantities of polydextrose and gentiobiose have approximately the same reducing power and assuming one reducing end-group per molecule.

The linkages which predominate in the polydextrose are primarily 1–6 but other linkages also occur. In the soluble polyglucoses each of the acid moieties is esterified to polyglucose. Where the acid moieties is esterified to more than one polyglucose moiety, cross-linking results.

The soluble polydextroses are useful for imparting physical properties of natural foods, other than sweetness, to dietetic foods from which natural sugars have been removed and replaced by artificial or other sweeteners. In baked goods, for example, the new polydextrose affect rheology and texture in a manner analogous to sugar and can replace sugar as a bulking agent. Typical uses for the soluble polydextroses are found in low calorie jellies, jams, preserves, marmalades and fruit butters, in dietetic frozen food compositions including ice cream, ice milk, sherbet and water ices; in baked goods such as cakes, cookies, pastries and other foodstuffs containing wheat or other flour; in icings, candy and chewing gum; in beverages such as non-alcoholic soft drinks and root extracts; in syrups; in toppings, sauces and puddings; in salad dressings and as bulking agents for dry low calories sweetener compositions containing cyclamate or saccharine.

The use of polydextrose provided by this invention allows the elimination of 20 to 100% of the normal fat, oil or fatty triglyceride components of the food. The degree of fat, oil or fatty triglyceride elimination will naturally vary with the type of food, for example, in a french salad dressing it is possible to completely eliminate the oily component normally included. In chocolate coatings, ice cream mixes and whipped toppings, 20 to 80% of the fat, oil or triglyceride can be eliminated while still retaining the required food characteristics such as texture, gloss, viscosity and taste of the food product.

As previously mentioned, aside from the replacement of sugar in many recipes there is an appreciable flour sparing and/or fat sparing effect that is possible without decreasing the quality of the food. The result is a further reduction in total calorie value of the food.

The term "fatty-triglyceride" refers to glycerol esters of the higher fatty acids contained in fats and oils. The use of the soluble polydextroses allows elimination of at least part of the fatty-triglyceride component of food. The degree of fatty-triglyceride elimination will naturally vary with the type of food.

In other types of food products, at least part of the carbohydrate ordinarily contained is replaced by soluble polydextroses. Also in some products at least part of the fatty-triglyceride and substantially all of the carbohydrate ordinarily contained is replaceable by soluble polydextrose.

The so-called fat-sparing effect is possible without decreasing the quality of the food in that the required food characteristics such as texture, gloss, viscosity and taste are still retained. Furthermore, the caloric value of these foods is lowered considerably by the fact that soluble polydextroses have been used to replace sugars and fatty-triglycerides which are contained in the natural counterparts of the dietetic foods.

In the traditional production of polydextrose, crude polymer was taken from the polymerization reaction and milled in order to provide a flowable powder useful in production of food products. This procedure has been described in U.S. Pat. No. 3,876,794 and U.S. Pat. No. 3,766,165. This milling procedure produces unwanted fines which are lost and/or discarded in order to provide polydextrose as a commercial commodity.

In the present invention, however, the contents of the reaction chamber is directed to a spinning head which includes a circumferential wall having openings through which feedstock can pass under centrifugal force as separate and distinct masses of polydextrose. The feedstock is metered to the spinning head at a rate which permits this polymerizate to be forced against the circumferential wall and permit separation of discrete portions of the mass as the feedstock melt is exposed to an opening in the wall. A heating element can be provided to maintain the polymer in flowable condition. A preferred embodiment contemplates the use of a heating element which provides controlled heating. The discrete masses are then cooled to form a solid product having the shape of flakes, fibers, spicules and other generally non-descript physical form which result from solidification while in free flow condition.

In an alternative embodiment, the molten material can be directed to a chamber in which the product is moved under pressure to an exit orifice. A stream of polydextrose is forced through the orifice and is subjected to a stream of fluid, gas or liquid, impacting the feedstock at a velocity which creates flash shear force. Apparatus with controlled heating can be used to maintain the flowability of the polymer from reactor to exit orifice. The force created by fluid impinging against the feedstock is referred to as disruptive fluid shear force.

Presently, the preferred fluid is air. However, the invention is not limited to the type of fluid used to create the disruptive fluid shear force.

In one embodiment, air is directed against the feedstock as a continuous high velocity jet. Another embodiment contemplates propelling the feedstock at high velocity against the force of an air atmosphere. In both cases the feedstock is abruptly disrupted into discrete discontinuous masses due to shear acting on the feedstock material while it has internal flow.

In the above flash shear process, a rapid cooling step is preferably used immediately following the shearing of the molten material into discrete masses to reduce discoloration or degradation. Preferably the discrete masses are immediately introduced into a cold gaseous environment such as that produced by refrigerated air, liquid carbon dioxide, liquid nitrogen and the like.

A characteristic of the product of the present invention is that the matrix resulting therefrom has a morphology which results from allowing flash disrupted feedstock to reform during free flow. This unique free-flow formation is achieved by preventing hindrance of continued flow while the material cooled to its original matrix structure.

In order to provide the new matrix material of the present invention, a unique apparatus has been devised which is able to deliver the feedstock from a reactor to a point where it is subjected to shear while in the internal flow conditions.

In FIG. 1 a block diagram is shown of the apparatus of the present invention wherein a reactor 10 is connected for fluid flow to a directing means 20 which maintains the contents of the polymerization reactant chamber in fluid flow condition for the next step of the apparatus. Finally, a means for applying shear force 30 is provided for shearing the feedstock and providing the novel polydextrose polymerizate.

Figure 2:
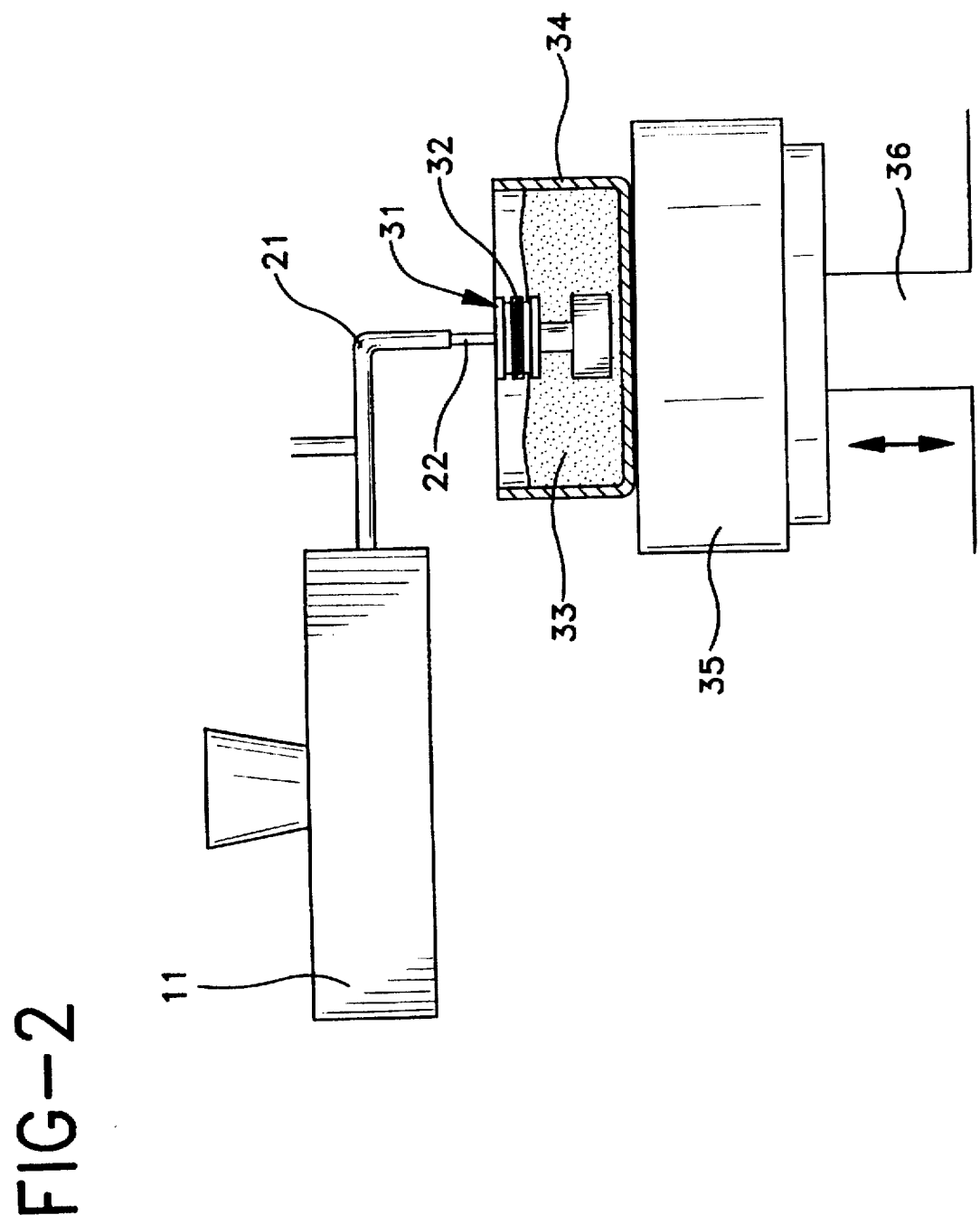
FIG. 2 is a schematic representation of one embodiment of the process and apparatus of the present invention.

In FIG. 2 a schematic representation of one embodiment of the invention has been shown wherein a reaction chamber 11 is provided for polymerizing the polydextrose. In fluid communication therewith is a transfer means 21 which maintains the contents of the reaction chamber in fluid flow condition for shearing. Finally, a means for shearing 31 is provided for receipt of the polydextrose melt 22 therein. Specifically, the shearing means 31 is a spinning head having openings 32 arranged around a circumferential wall 33 through which the polydextrose is separated and flung outwardly under centrifugal force during spinning. A heating element, such as a heating band or ribbon, can be provided around the circumference of the head to maintain the polydextrose in flowable condition. Polydextrose moves under centrifugal force through the heating element and opening 32 and is caught in a bin 34. The bin 34 can be lowered by means of platform 35 arranged on lift means 36. The lift means 36 can be raised and again positioned for receipt of polydextrose.

Figure 3:
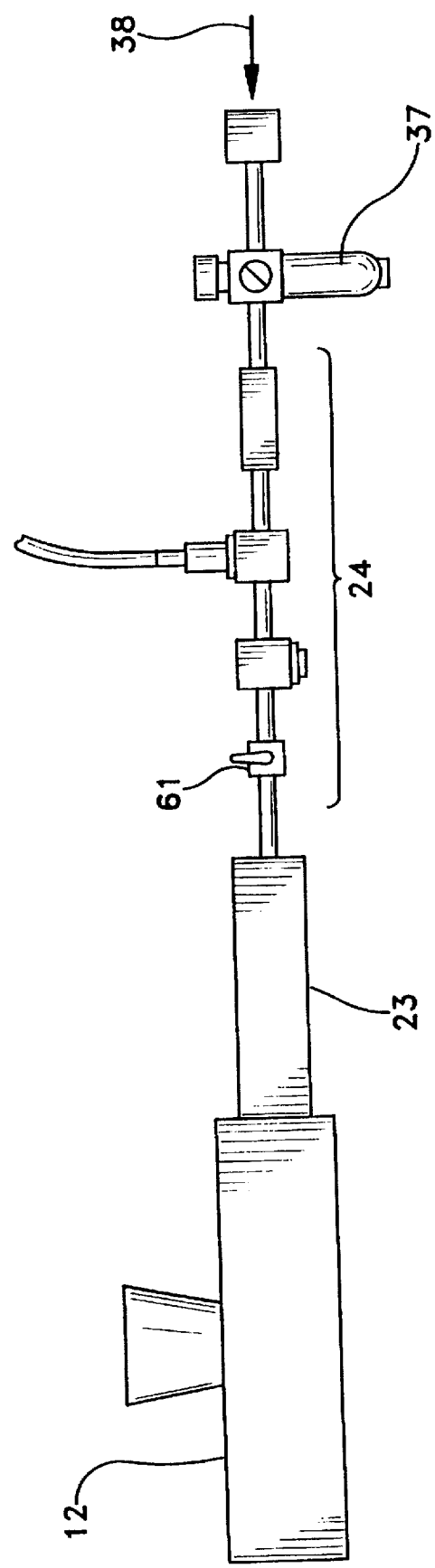
FIG. 3 is a schematic drawing of yet another embodiment of the process and apparatus of the present invention.

In FIG. 3, a reaction chamber 12 is provided for polymerizing polydextrose and is in direct fluid communication with a extruder feeder 23. The extruder feeder 23 advances the contents of the reaction chamber 12 through to an exit connecting means 24. The extruder and connecting means 24 control the temperature, pressure and moisture content of the throughput before being introduced to a nozzle 37 which provides the shearing effect for producing the novel polydextrose polymerizate. In order to provide disruptive fluid shear force, high velocity heated air 38 is directed to the nozzle 37.

Figure 4:
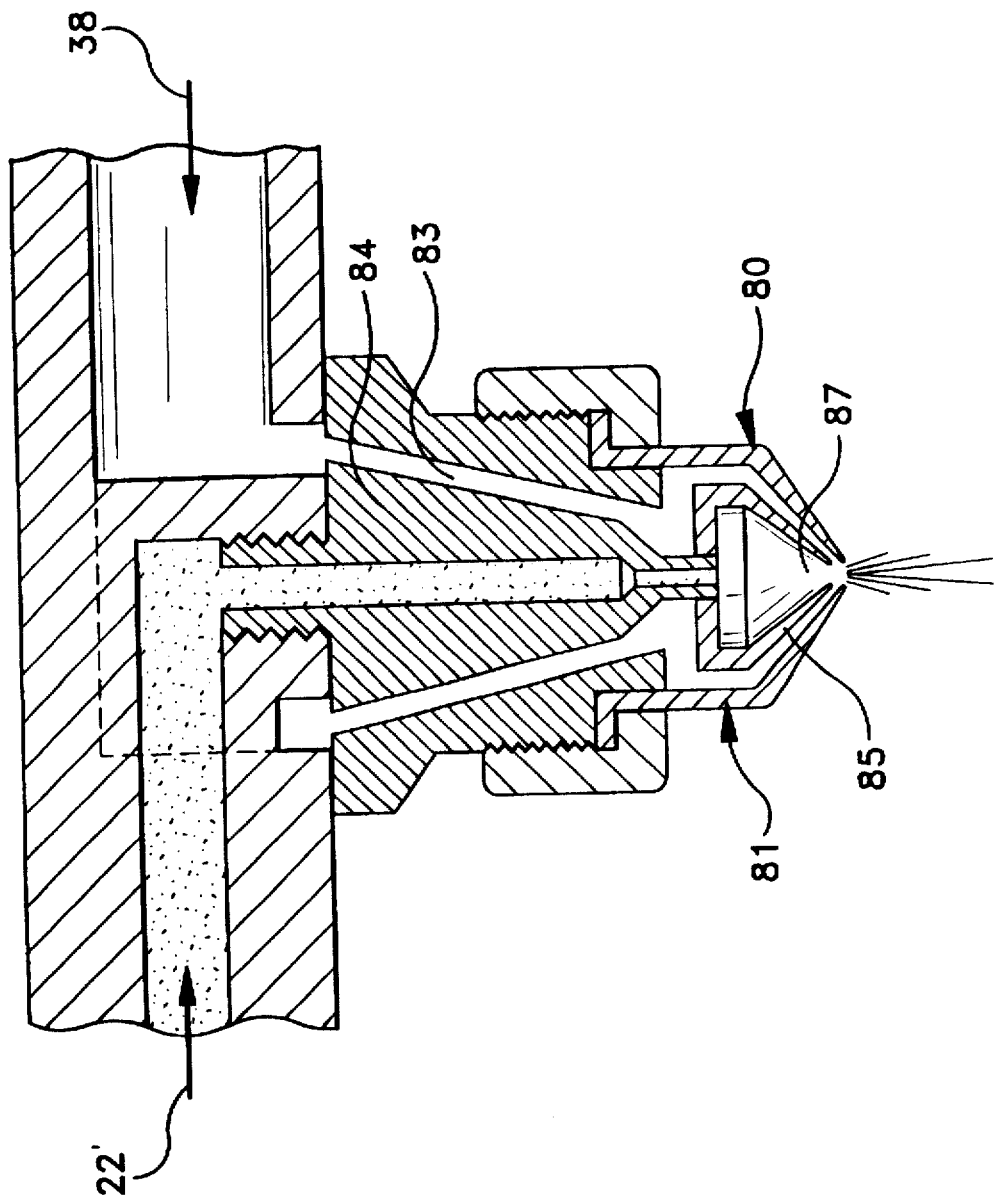
FIG. 4 is a schematic drawing of a shear nozzle which can be used in the embodiment shown in FIG. 3.

Referring to FIG. 4, a stream of air 38 can be seen being directed against the feedstock exterior of the nozzle to provide discontinuities in the feedstock and permit a morphology to be achieved by free-flow solidification as discontinuous masses. In FIG. 4, the air stream 38 is seen in fluid communication with annular chamber 83 which surrounds the internal nozzle device 84. Feedstock 22' is fed to the nozzle and exits as a coherent stream 87 where it is subjected to high-velocity air stream 85. The high-velocity air stream 85 is created by tortuous path exit route provided by air cap 80 and retaining ring 81.

Other measures can be taken to ensure that the internal flow condition created in the extruder/heater is not lost by heat transfer as the feedstock is advanced to the point of shear and beyond to permit free-flow formation. For example, valve mechanism 61 can be heated to eliminate transfer of heat from the feedstock to a relatively cooler valve mechanism. Moreover, heat can be maintained at the point of shear, generally identified by elements 80 and 81, by directing a heatgun at them during operating or by using a temperature controlled heating band. Alternatively, the temperature of the internal nozzle 84 can be raised or lowered relative to the stream of heated air to prevent transfer of heat from the feedstock and consequent cooling below flow conditions. As the process continues, however, a steady-state temperature of each of the mechanisms will be attained so that additional heat to individual elements of the operations is not required to prevent undue heat transfer and cooling.

When air is used to create the shear force, it is applied in a two-fluid nozzle at a pressure of from about 1.5 to about 20 atmospheres. Preferably, the pressure is applied at about 2 atmospheres to 10 atmospheres. The temperature of the air used to create the shear force should preferably be controlled to a temperature at least about 0.1° C. above the temperature of the feedstock being ejected for every atmosphere of pressure.

Oleaginous material can be added before or after polymerization. The oleaginous substance can be a food-acceptable/edible oil. Such substances are selected from vegetable oils, soybean oil, canola oil, corn oil, sunflower oil, olive oil, mixtures thereof and the like. In this aspect, the oils are preferably low in saturated fats.

The particles produced in the flash shear processes generally have a morphology which differs from that of the ground powders obtained in previous processes. The flash shear polydextrose can be produced as flakes, fibers, (including hollow fibers) and spicules.

The oleaginous can be a fat such as an edible animal fat or fatty material. For example, beef, pork, lamb or similar animal fats or mixtures thereof may be used. Similarly, fat containing materials such as beef tallow, sheep tallow, butter or lards, hydrogenated animal and/or vegetable oils may be included. Moreover, fish or crustacean-based oils or oleaginous materials are also useful. Combinations of the above-described oleaginous materials are also contemplated.

Another aspect of the present invention is the ability to include at least one additional material with the polydextrose such as bioaffecting agents. Categories of such ingredients may vary widely. Illustrative categories and specific examples include:

(a) Antitussives, such as dextromethorphan, and chlorphedianol hydrochloride;

(b) Antihistamines, such as chlorpheniramine maleate and terfenadine;

(c) Decongestants, such as phenylephrine, phenylpropanolamine, pseudoephedrine and ephedrine;

(d) Various alkaloids, such as codeine and morphine;

(e) Mineral supplements such as potassium chloride;

(f) Laxative, vitamins and antacids;

(g) Ion-exchange resins such as cholestyramine;

(h) Anti-cholesterolemic and anti-lipid agents;

(i) Antiarrhythmics such as N-acetyl-procainamide;

(j) Antipyretics and analgesics such as acetaminophen, aspirin and ibuprofen;

(k) Appetite suppressants such as phenylpropanolamine hydrochloride or caffeine;

(l) Expectorants such as guaifenesin;

(m) Anti-anxiety agents such as diazepam; and (n) Anti-ulcer agents such as sucralfate.

A non-limiting list of other active ingredients includes anti-inflammatory substances, coronary dilators, cerebral dilators, peripheral vasodilators, antiinfectives, psychotropics, antimanics, stimulants, gastrointestinal agents, sedatives, antidiarrheal preparations, anti-anginal drugs, vasodialators, anti-hypertensive drugs, vasoconstrictors, migraine treatments, antibiotics, tranquilizers, antipsychotics, antitumor drugs, anticoagulants, antithrombotic drugs, hypnotics, antiemetics, anti-nauseants, anticonvulsants, neuromuscular drugs, hyper- and hypoglycemic agents, thyroid and antithyroid preparation, diuretics antispasmodics, uterine relaxants, mineral and nutritional additives, antiobesity drugs, anabolic drugs, erythropoietic drugs, antiasthmatics, cough suppressants, mucolytics, anti-uricemic drugs, and mixtures thereof.

The medicaments contemplated herein are particularly well-suited for use when it is desired to disperse the agent in aqueous liquids and/or mask cover the undesirable tastes of actives. The flavor of unpleasant medicaments can also be masked or altered if desired by adding a flavoring agent and/or a sweetening agent to the pre-spun mixture.

In an alternative aspect of the invention, the adjuvant materials included with the polydextrose are cosmetic-related ingredients. Cosmetic ingredients are those materials which have a skin beautifying and/or complexion-related activity. Such products can be used externally on hair, skin or both. A non-limiting list of ingredients which have appearance-improving cosmetic activity includes dimethyl siloxanes, mucopolysaccharides, methyl and propyl parabens, biotin, lanolin, aloe, glycerin, mineral oil, nicotinamide compounds, sun screens, such as para-aminobenzoic acid, hair conditions, moisturizers, moisturizing creams, astringents, powders such as talcs and combinations thereof.

It will be understood by those skilled in the art from the present description that additional materials can be included with the polydextrose and principle active ingredients. Thus, colors, flavorants, fragrances, dyes, pigments, antioxidants, preservatives and similar ingredients can be added in both the matrix and product in which the matrix is included. Such materials serve to improve the appearance, aroma, shelf-life or other properties of the products prepared and described herein. Moreover, the final products can also contain those adjuvant materials which are particularly suited for particular end uses.

Flavorants can include sweeteners, both synthetic and natural, and other flavor ingredients, such as flavor oils or essences. These oils are generally derived from plant extracts, although they may also be synthetically derived. Peppermint oil, spearmint oil, cinnamon oil, oil of wintergreen, citrus oils and other fruit essences are the most commonly used flavor oils which are employed in the present invention. Examples of citrus or first oils and/or essences which are useful include a host of materials such as apple, apricot, banana, blueberry, cherry, grape, grapefruit, lemon, lime, orange, pear, peaches, pineapple, plum, raspberry, strawberry and the like. Mixtures and derivatives of these oils are contemplated.

Additional flavorants can be chosen from synthetic flavor oils and flavoring aromatics, and/or oils, oleo resins and extracts derived from plants, leaves, flowers, furits and so forth, and combination thereof. For example, clove oil, bay oil, anise oil, eucalyptus oil, thyme oil, cedar leaf oil, oil of nutmeg, oil of sage, oil of bitter almonds and cassia oil may be used. Commonly used flavors include menthol, artificial vanilla, cinnamon derivatives, and various fruit flavors, whether employed individually or in admixture.

Flavorings such as aldehydes and esters including cinnamyl acetate, cinnamaldehyde, citral diethylacetal, dihydrocarvyl acetate, eugenyl formate, p-methylamisol, and so forth may also be used. Generally any flavoring or food additive such as those described in "Chemicals Used in Food Processing," pub. 1274 by the National Academy of Sciences, pages 63–258 may be used.

Further examples of aldehyde flavorings include, but are not limited to acetaldehyde (apple); benzaldehyde (cherry, almond), anisic aldehyde (licorice, anise); cinnamic aldehyde (cinnamon); citral, i.e., alpha citral (lemon, lime); neral, i.e. beta citral (lemon, lime); decanal (orange, lemon); ethyl vanillin (vanilla, cream),; hellotropine, i.e., piperonal (vanilla, cream); vanillin (vanilla, cream); alpha-amyl cinnamaldehyde (spicy fruity flavors); butyraldehyde (butter, cheese); valcraldehyde (butter, cheese); citronellal; decanal (citrus fruits); aldehyde C-8 (citrus fruits); aldehyde C-9 (citrus fruits); aldehyde C-12 (citrus fruits); 2-ethylbutyraldehyde (berry fruits); hexenal, i.e., trans-2 (berry fruits); tolyl aldehyde (cherry, almond), veratraldehyde (vanilla); 2,6-dimethyl-5-heptenal, i.e. Melonal (melon); 2,6-dimethyl-5-heptenal, i.e. Melanal (melon); 2,6-dimethyloctanal (green fruit); and 2-dodecenal (citrus, mandarin); cherry; grape; strawberry shortcake; mixtures thereof; and the like.

Other specific flavor compounds such as ethylacetate, thiophene ethylpropionate, ethyl butyrate, 2-hexanoate, 2-methylpyazine, hiptaldehyde, 2-octanone, limonene, and eugenol are useful.

The nature and amount of all materials included in the matrix will vary greatly. The amount of active material included in the product will depend upon the active ingredient and the amount required to achieve a desired therapeutic and/or cosmetic effect.

In further aspects of the invention, supplemental materials such as bioadhesives, dispersants, surfactants and the like can be included. For example, bioadhesive-type materials such as hydrogels or synthetic materials such as polyvinylpyrrolidone are useful. Dispersants such as polyacrylates and alginates are also useful.

A-non-limiting list of surfactants which are useful in combination with the matrix of the invention include as follows: anionic surfactants such as alkyl carboxylates, alkyl sulfates, ethoxylated alkyl sulfates, sulfosuccinate esters, isothionates, sarcosinates, sodium lauryl sulfoacetates, fatty acid-polypeptide condensates, linear alkyl arylsolfonates (LAS), alpha-olefin sulfonates (AOS), organic phosphate esters; cationic surfactants such as sodium lauryl sulfate (SLS), cetrimonium bromide and polysorbates; amphoteric surfactants such as alkylamino propionates, acyl ethylenediamines and betaines; non-ionic surfactants such as ethoxylated and propoxylated derivatives and polyol esters including sorbitan esters polyoxyethylene ethers; alkyl polyglycosides, sulfonic acid/linear alkylate sulfonates, silicon derived phosphate esters, non-oxynol surfactans, Triton™ surfactants and alkylphenols.

The various ingredients added to the polydextrose can be added by various means including introduction into static mixers in the flow path or introduction into high shear mixers in the flow path. Where the ingredient is sensitive to degradation at the temperatures of the molten polydextrose the ingredients are added just prior to the flash shear step.

In a preferred embodiment wetting agents are added to the polydextrose prior the flash shear step, preferably in amounts of less than 5% by weight. Particularly useful wetting agents include lecithin, maltodextrins (including corn syrup solids), fructose, glucose, honey, hydrogenated honey, inositol, sucrose, sodium prryolidone carboxylic acid, lactic acids, polyethylene glycols, glycerin, polyols such as, propylene glycol, glycerol, sorbitol, mannitol, xylitol and platinit and the surfactants mentioned above. The discrete particles made with such wetting agents have improved dispersibility especially when large volumes of polydextrose are added to aqueous medium. In many instances clumping of the dry solids often encountered with polydextrose solids is substantially eliminated.

The following examples serve to provide further appreciation of the invention, but are not meant in any way to restrict the effective scope of the invention. In examples in which spinning is used, reference is made to copending commonly-owned U.S. application Ser. No. 954,257, filed Sep. 30, 1992 and in general apparatus such as those adapted to produce cotton candy or floss from sugar. Illustrative of such machine is the Econo Floss Machine Model 3017 manufactured by Gold Metal Products Company of Cincinnati, Ohio. It will be appreciated by those skilled in the art that any apparatus or physical process which provides similar shear force and time/temperature gradient conditions can also be used. Similarly, when disruptive fluid shear force is mentioned, the phenomena described in copending commonly-owned application bearing Ser. No. 965,804 filed on Oct. 23, 1992 is referred to. By reference to these processes, the preferred embodiments of the present invention can be better described.

PRELIMINARY EXAMPLE

In order to verify the ability to produce a shearform product from molten polydextrose, an experiment was run wherein a melted stream of polydextrose was directed from an extruder into a dual ribbon spinning head. A white floss was produced which has excellent color and texture characteristics.

The examples set forth herein describe full implementation of the invention.

EXAMPLES

Example 1

In this example, an insoluble polydextrose is prepared which shall be referred to in subsequent examples for purposes of explaining the process of the present invention. In particular, dried white, crystalline, refined dextrose (pure monosaccharide), in anhydrous form and powdered citric acid are mixed at a ratio of 16:1, and is reacted while stirring under a pressure of 14 mm. of Hg. The melt is maintained at 170° centigrade for 25 hours in order to complete polymerization. The charge resulting from this reaction is used in further examples set forth herein to produce the novel polymerizate resulting from the present invention.

Example 2

In Example 2 a water soluble polydextrose feedstock is prepared by contacting powdered anhydrous glucose and citric acid at a ratio of 39:1. The mixture is intimately mixed and reacted at 160° centigrade at a reduced pressure of 0.1 mm of Hg for 8 hours. This product is used later as a charge for producing the novel polymerizate of the present invention.

Example 3

The reactor charge resulting from Example 1 is directed to a spinning apparatus operating at a speed of approximately 3500 RPM. The operating temperature of the head is approximately 140° to 150° centigrade. The molten material resulting from the polymerization reaction is metered to the spinning head at a rate which permits the material to be flung outwardly against the circumferential wall of the spinning head and forced by centrifugal force through openings provided in the head to separate and permit free flow formation of discrete polydextrose masses. The rate of introducing the material to the head is such that it is not permitted to solidify or crystallize before it completes the process of the present invention.

White spicule-like flakes are expected as a result of the present process. These flakes are easily handled and readily dispersible in other masses such as food ingredients.

Example 4

The contents of the reactor in Example 1 are in fluid communication with a chamber which advances the material throughput under pressure to a exit nozzle. The reaction mixture is forced through the exit nozzle under pressure to be met by a stream of heated high velocity air which creates flash disruptive shear force on the feedstock. The flash disrupted feedstock is permitted to form as discreet masses during free-flow to attain an original polymerizate morphology.

The expected polydextrose polymerizate is substantially white in color and has a light flaky texture. This material is easily adaptable for many uses and can be conveniently packaged as a commercial commodity for distribution, sale, and use.

Example 5

The reactor charge resulting from Example 2 is directed to a spinning apparatus operating at a speed of approximately 3500 RPM. The operating temperature of the head is approximately 140° to 150° centigrade. The molten material resulting from the polymerization reaction is metered to the spinning head at a rate which permits the material to be flung outwardly against the circumferential wall of the spinning head and forced by centrifugal force through openings provided in the head to separate and permit free flow formation of discrete polydextrose masses. A heating band is positioned adjacent to the outer wall to provide the effective extrusion orifice. The heating band is heated to compensate for any cooling of the spinning apparatus and to maintain an extrusion oriface at the flow temperature of the polydextrose. The rate of introducing the material to the head is such that it is not permitted to solidify or crystallize before it completes the process of the present invention.

White spicule-like flakes are expected as a result of the present process. These flakes are easily handled and readily dispersible in other masses such as food ingredients.

Example 6

The contents of the reactor in Example 2 are in fluid communication with a chamber which advances the material throughput under pressure to a exit nozzle. The chamber is provided with controlled heating to maintain flowable conditions. The reaction mixture is forced through the exit nozzle under pressure to be met by a stream of heated high velocity air which creates flash disruptive shear force on the feedstock. The flash disrupted feedstock is permitted to form as discreet masses during free-flow to attain an original polymerizate morphology.

The expected polydextrose polymerizate is substantially white in color and has a light flaky texture. This material is easily adaptable for many uses and can be conveniently packaged as a commercial commodity for distribution, sale, and use.

Thus, while there have been described what are presently believed to be the preferred embodiments of the present invention, those skilled in the art will realize that other and further modifications can be made without departing from the true spirit of the invention, and it is intended to include all such modifications and variations as come within the scope of the claims as set forth below.

I claim:

1. A process for polymerizing polydextrose comprising
   polymerizing anhydrous glucose and maltose in the absence of added water to produce anhydrous flowable polydextrose melt,
   maintaining said melt as a flowable melt, and
   subjecting a stream of said anhydrous flowable polydextrose polymerizate melt resulting from said anhydrous melt polymerization to a shear force which separates said stream into multiple masses of polydextrose matrix under conditions which induce solidification under free flow condition immediately after shearing to provide separate masses of polydextrose polymerizate in the absence of milling.

2. The process of claim 1 wherein said stream of anhydrous flowable polymerizate is subjected to shear force by directing said stream of flowable polydextrose polymerizate from a reactor where said stream of polydextrose is produced to a spinning apparatus which provides shear force and separation whereby said separate solid polydextrose masses are formed.

3. The process for claim 1 wherein said stream of anhydrous flowable polymerizate is subjected to shear force by directing said stream of flowable polydextrose polymerizate from a reactor where said anhydrous polydextrose is produced under pressure to an exit orifice and applying disruptive fluid shear force which separates said stream of polymerizate into separate masses of polydextrose.

4. The process of claim 1 wherein said stream of polymerizate is maintained at flowable condition by addition of heat prior to being subjected to said shear force.

5. The process of claim 1 which further comprises introducing at least one additional ingredient to said polymerizate prior to subjecting said stream of polymerizate to said shear force whereby said masses include said at least one additional ingredient.

6. The process of claim 5 wherein said additional ingredient is a wetting agent.

7. The process of claim 6 wherein said wetting agent is sorbitol.

* * * * *